United States Patent [19]

Wada et al.

[11] 4,277,150
[45] Jul. 7, 1981

[54] EYE REFRACTMETER

[75] Inventors: Shinzi Wada; Ikuo Kitao; Yasuo Kato; Taketoshi Ishihara, all of Tokyo, Japan

[73] Assignee: Tokyo Kogaku Kikai Kabushiki Kaisha, Tokyo, Japan

[21] Appl. No.: 935,608

[22] Filed: Aug. 21, 1978

[30] Foreign Application Priority Data

Aug. 24, 1977 [JP] Japan ............................. 52-101239
Aug. 24, 1977 [JP] Japan ............................. 52-101240
Feb. 3, 1978 [JP] Japan ............................. 53-12192[U]
Feb. 4, 1978 [JP] Japan ............................. 53-11610

[51] Int. Cl.³ .................. G03B 29/00; A61B 3/14; A61B 3/10
[52] U.S. Cl. .................................... 351/13; 351/7; 354/62
[58] Field of Search ................. 351/7, 6, 13, 9, 16; 354/62

[56] References Cited

U.S. PATENT DOCUMENTS

| | | | |
|---|---|---|---|
| 2,586,973 | 2/1952 | McMillin | 351/7 |
| 3,572,909 | 3/1971 | Van Pattern et al. | 351/16 X |
| 3,864,030 | 2/1975 | Cornsweet | 351/7 |
| 3,871,772 | 3/1975 | Munnerlyn et al. | 351/13 X |
| 3,880,501 | 4/1975 | Munnerlyn | 351/13 X |
| 3,883,233 | 5/1975 | Guilino | 351/13 X |
| 4,098,549 | 7/1978 | Matsumura | 351/6 X |
| 4,146,310 | 3/1979 | Kohayakawa | 351/7 |

OTHER PUBLICATIONS

Mohrman et al., Putting the Knife Edge to the Eye, Optical Engineering, Jul. 1976.

Primary Examiner—John K. Corbin
Assistant Examiner—Rodney B. Bovernick
Attorney, Agent, or Firm—Stevens, Davis, Miller & Mosher

[57] ABSTRACT

An eye refractmeter comprising a target projecting optical system for projecting an image of a target means through a pupil of a patient's eye to produce a target image on a retina of the eye, an observing optical system including objective lens means for observing the target image through the pupil, and a sighting optical system for observing light reflected at the cornea of the eye to determine that the objective lens means is appropriately spaced from the patient's eye, means being provided in the projecting optical system so that the image of the target means is projected by an infrared ray, half-transparent optical means for passing therethrough one of the light bundles along the observing and sighting optical systems and reflecting the other of the bundles, means for directing both of the light bundles passing through the observing and sighting optical systems to a single image pick-up tube, the half-transparent optical means having a reflecting rate such that more than 50% of the light along the observing optical system and less than 50% of the light along the sighting optical system are directed to the image pick-up tube.

13 Claims, 10 Drawing Figures

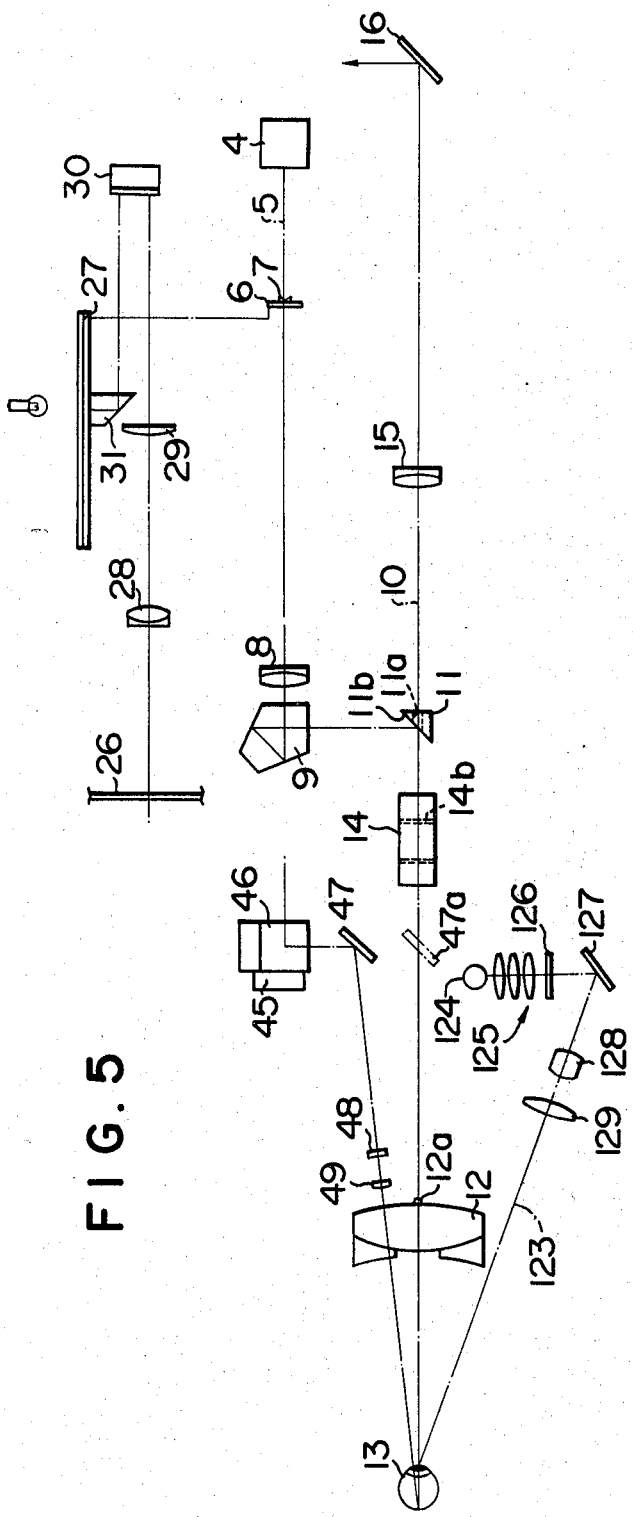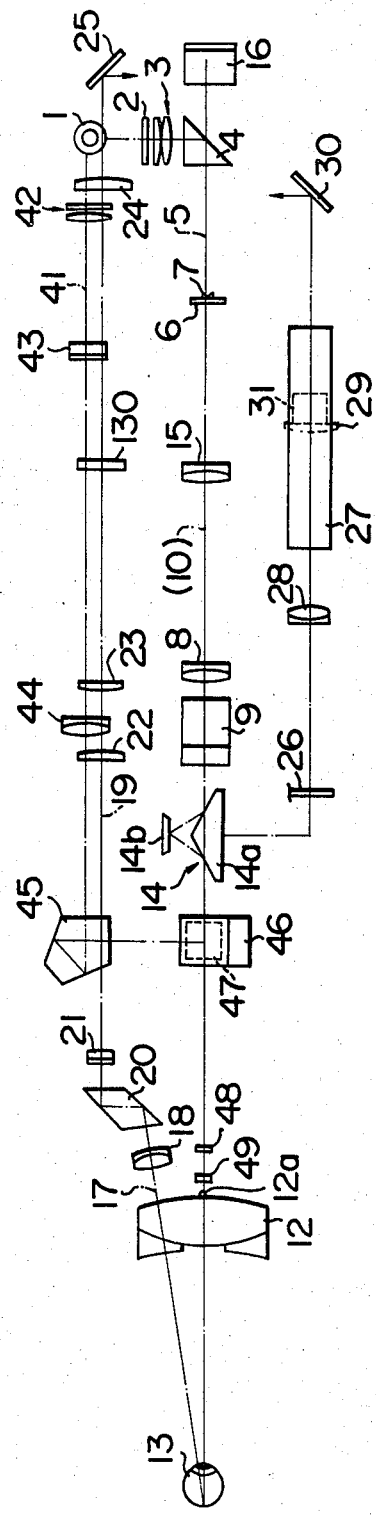

EYE REFRACTMETER

The present invention relates to eye refractmeters for determining refractive powers or correcting dioptral values of patient's eyes through observations of target images projected through pupils on retina of the patient's eye.

This type of refractmeter generally includes a projecting optical system for projecting a target image through the pupil of the patient's eye, and an observing optical system for observing the target image on the retina of the eye. Means is provided for moving the target along the optical axis of the projecting system so that a clear image of the target is obtained on the retina. The position of the target is therefore considered as representing the refractive power of the patient's eye which is then measured in terms of the correcting dioptral value in accordance with the position of the target. For the purpose of observation, there is therefore provided a scale projecting system which projects an indication of the target position in terms of the correcting dioptral value. Means is further provided in order to make it possible to determine the astigmatic axis for rotating the target image about the optical axis of the projecting system. The angle of rotation of the target image is also projected by the scale projecting system for visual observation.

For the observation by the refractmeter, it is required to maintain a predetermined distance between the objective lens of the refractmeter and the patient's eye. For this purpose, the refractmeter is provided with a sighting optical system for observing the light reflected at the cornea surface.

In such refractmeters, when the target projection is carried out by means of a visual ray, the patient's eye may be dazzled which may influence the results of measurements. Therefore, it is desirable to use an infrared ray for the purpose of the target projection. However, in order to use such infrared ray in the target projection, the observing and sighting optical systems must be provide with noctovision means including image pick-up tubes. If the arrangement is such that the light bundles in both the observing and sighting optical systems are directed to a single image pick-up tube, the light bundles have to be passed through the focusing lens with relatively large incident angles in order to avoid overlapping of lenses and light bundles. Therefore, inconveniencies are encountered in that the image of the observing bundle and that of the sighting bundle are unnecessarily spaced apart from each other on the photoelectric surface of the image pick-up tube. This is also true in the case of the scale projecting bundle.

It is therefore an object of the present invention to eliminate the aforementioned problems of an eye refractmeter in which the target projection is carried out by an infrared ray and the light bundles passing through the observing and sighting optical systems are directed to a single image pick-up tube so as to make it possible to observe the images by using such a single image pick-up tube.

Another object of the present invention is to provide an eye refractmeter in which the light bundles passing through the observing and sighting optical systems are directed to a single image pick-up tube with properly balanced intensities.

A further object of the present invention is to provide an eye refractmeter in which means is provided to make the projected target invisible while maintaining the intensity of light bundles at a suitable level.

A still further object of the present invention is to provide an eye refractmeter including a viewing mark for maintaining the patient's eye in a condition seeing an infinitely far point.

A yet further object of the present invention is to provide an eye refractmeter including a sighting optical system which can establish an exact alignment of the optical axis of the patient's eye and that of the observing system.

According to the present invention, the above and other objects can be accomplished by an eye refractmeter comprising a target projecting optical system for projecting an image of target means through a pupil of a patient's eye to produce a target image on retina of the eye, an observing optical system including objective lens means for observing the target image through the pupil, and a sighting optical system for observing light reflected at the cornea of the eye to determine that the objective lens means is appropriately spaced from the patient's eye, means being provided in said projecting optical system so that the image of the target means is projected by an infrared ray, half-transparent optical means for passing therethrough one of light bundles along said observing and sighting optical systems and reflecting the other of the bundles, means for directing both of the light bundles passing through said observing and sighting optical system to a single image pick-up tube, said half-transparent optical means having a reflecting rate such that more than 50% of the light along the observing optical system and less than 50% of the light along the sighting optical system are directed to the image pick-up tube.

Preferably, the arrangement should be such that approximately 90% of the light bundle along the observing optical system and approximately 10% of the light bundle along the sighting optical system are directed to the image pick-up tube. It is also preferable that the light through the observing optical system is passed through the half-transparent optical means while the light through the sighting optical system is reflected by the half-transparent optical means.

In this type of eye refractmeter, if the projected target image is visible to the patient, self-adjustments may be made unconsciously by the patient so that the results of measurements may be affected. In order to avoid such problems, it is preferable to project the target image by using an infrared ray. More preferably, in order for maintaining the patient's eye in a condition seeing an infinitely far point, a viewing mark is projected by a parallel light bundle and the target image is projected around the mark so that the patient's attention is directed only to the viewing mark.

The above and other objects and features of the present invention will become apparent from the following descriptions of preferred embodiments taking reference to the accompanying drawings, in which;

FIG. 4 is a plan view of the optical system shown in FIG. 1;

FIG. 5 is a side view of the optical system shown in FIG. 1;

FIGS. 6 and 7 show examples of projected target image;

Figure 1:
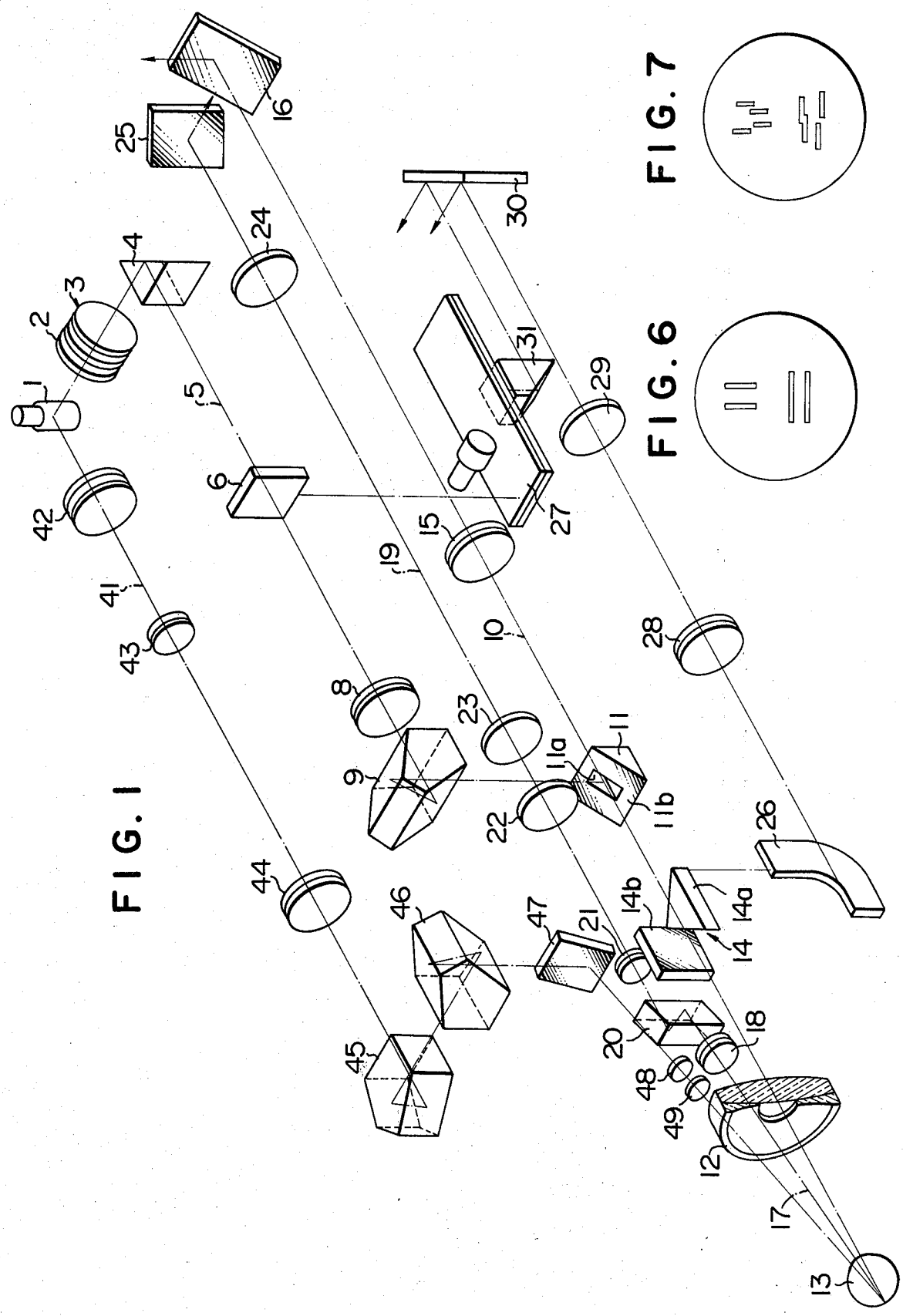
FIG. 1 is a perspective view showing the optical system of an eye refractmeter in accordance with one embodiment of the present invention.

Referring now to the drawings, particularly to FIGS. 1 through 5, the refractmeter shown therein includes a target projecting optical system comprising a light source 1 from which light is passed through a filter 2 which is transparent to an infrared ray and then through a collimater lens 3. The light is passed from the lens 3 in the form of a parallel light bundle and reflected by a prism 4 along a projecting optical axis 5. On the axis 5, there is disposed a target 6 which has a target pattern such as that shown in FIG. 6. On the target 6, there is provided an image splitting device 7 such as a crossed-wedge shaped prism assembly. Along the projecting optical system there are also provided a lens 8 and a pentagonal prism 9 which functions to reflect the projecting light downwardly.

Beneath the projecting optical axis 5, there is an observing optical axis 10 and the reflecting optical axis from the prism 9 intersects the axis 10. At the intersection of the axes, there is provided an apertured prism 11 having an aperture 11a coaxial with the optical axis 10 and a reflecting surface 11b for reflecting the projecting light bundle forwardly along the optical axis 10. The projecting light which has been reflected by the reflecting surface 11b of the prism 11 is projected through an objective or projecting lens 12 to a patient's eye 13. The projected light is passed through the pupil of the eye 13 and produces an image of the target on the retina of the eye.

Between the apertured prism 11 and the projecting lens 12, there is disposed an image rotating device 14 which is comprised of a triangular prism 14a and a planar reflecting mirror 14b opposing to the apex of the prism 14a. A rotation of the device 14 about the optical axis 10 causes a rotation of the target image projected through the lens 12.

The target image produced on the retina of the patient's eye is observed by the observing optical system which includes a lens 15 and a reflecting mirror 16 disposed along the optical axis 10 behind the apertured prism 11. Thus, the light reflected at the retina of the eye is passed through the objective lens 12, the image rotating device 14 and the aperture 11a of the prism 11 to the lens 15 from which it is further passed to the reflecting mirror 16 which functions to reflect the light upwardly.

The illustrated refractmeter includes a sighting optical system for determining an exact distance between the lens 12 and the patient's eye 13. The sighting optical system includes a lens 18 disposed behind the objective lens 12 along an optical axis 17 which is inclined with respect to the optical axis 10 and directed through the objective lens 12 to the patient's eye 13. There is further provided a prism 20 which functions to direct the light which has passed through the lenses 12 and 18 along an optical axis 19 extending parallely with respect to the optical axis 10. Along the optical axis 19, there are provided a series of lenses 21, 22, 23 and 24 and the light through the lenses is reflected laterally by a reflecting mirror 25.

The scale projecting system includes an angular scale 26 which is interconnected with the image rotating device 14 to rotate therewith and a dioptral scale 27 which is interconnected with the target 6 to move therewith. The angular scale 26 is projected through lenses 28 and 29 and reflected laterally by a mirror 30. The dioptral scale 27 is projected through a prism 31 and reflected laterally by the mirror 30.

Figure 2:
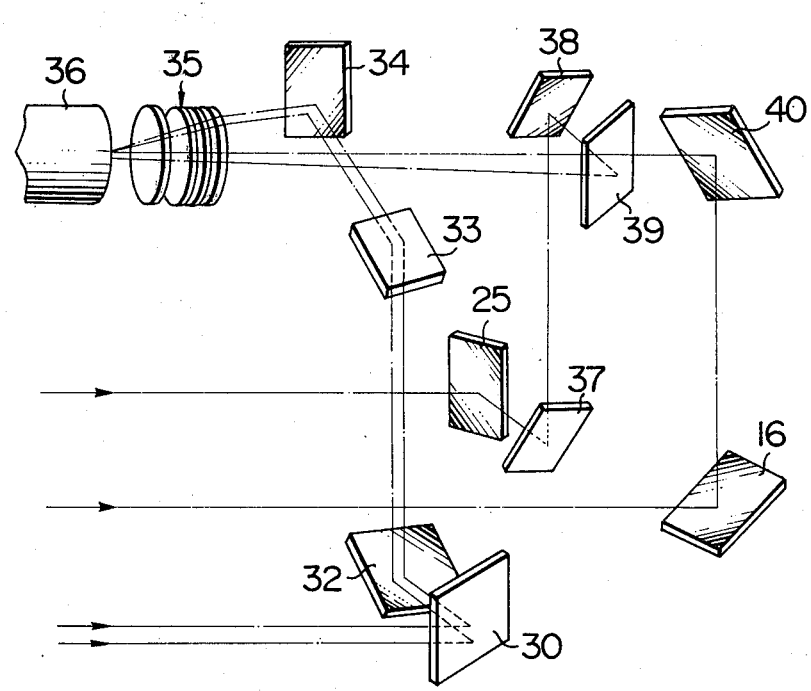
FIG. 2 is a perspective view showing the arrangement of optical elements for directing light bundles to a single image pick-up tube.
Figure 3:
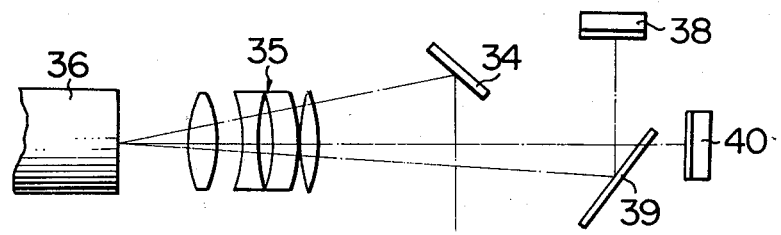
FIG. 3 is a plan view of the arrangement shown in FIG. 2.

Referring to FIGS. 2 and 3, it will be noted that the scale projecting light bundles which have been reflected by the mirror 30 are reflected upwardly by a further reflecting mirror 32, then laterally by a mirror 33 and thereafter by a mirror 34 to pass through a focusing lens 35 to a photoelectric surface on an image pick-up tube 36.

It should further be noted that the sighting light bundle which has been reflected by the mirror 25 is again reflected upwardly by a reflecting mirror 37 and then laterally by a reflecting mirror 38. Thereafter, the light bundle is reflected at a reflecting surface of a half-transparent mirror 39 and passed through the focusing lens 35 to the image pick-up tube 36.

The observing light bundle which has been reflected upwardly by the mirror 16 is then reflected by a mirror 40 and thereafter passed through the half-transparent mirror 39 and the focusing lens 35 to the image pick-up tube 36.

In the projecting optical system, the projection of the target is made by using an infrared ray, preferably those portions of infrared ray having wave lengths close of those of visible light, so that infrared rays are passed through the observing and sighting optical systems. Visible light is used to project the scales. Therefore, the image pick-up tube as used herein has a sensitivity both to the infrared ray and the visible light.

The observing optical system is designed to pass the light as reflected at the retina of the patient's eye while the sighting optical system receives the light reflected at the eyelid, the conjunctiva and the iris, so that the intensity of the light through the sighting system is much greater than that through the observing system. According to the present invention, the half-transparent mirror 39 is so designed that it has less than 50% of rate of reflection whereby a greater percentage of light through the observing optical system is led to the image pick-up tube 36. Preferably, the rate of reflection of the half-transparent mirror 39 should be less than 10%. It is of course possible to design the system in such a manner that the light through the observing system is reflected by the half-transparent mirror 39 and the light through the sighting system is passed through the half-transparent mirror 39. In such an arrangement, the half-transparent mirror 39 shall have more than 50%, preferably approximately 90% of the rate of reflection.

The target image produced by the projecting optical system on the retina will be correctly focused as shown in FIG. 6 when the patient's eye has a normal refractive power. However, in case where the patient's eye 13 is short or long-sighted, the target image will be split as for example shown in FIG. 7. In this instance, the target 7 is moved along the projecting optical axis 5 until a correctly focused image is produced. The position of the target 7 along the axis 5 is designated on the scale 27 in terms of the corrective dioptral value and the value is projected on the image pick-up tube through the scale projecting system. For inspecting the astigmatism, the target image is observed while the image rotating device 14 is being rotated to find out the orientation of the astigmatic axes. The astigmatic axes are then designated in terms of an angle.

Figure 8:
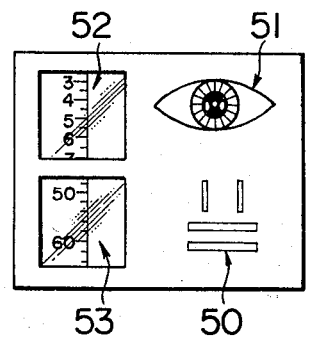
FIG. 8 shows an example of video display.

Referring to FIG. 8, there is shown an example of images displayed on a video tube in accordance with the inputs of the image pick-up tube 36. The target image as obtained through the observing system is shown by the reference numeral 50, the image of the cornea as obtained through the sighting system by 51, the dioptral value of the scale system by 52 and the angle of the astigmatic axis by 53.

Where the image pick-up tube is provided with means for maintaining the total intensity of photoelectric current constant throughout the photoelectric surface thereof, there is a tendency that the sensibility of the photoelectric surface is decreased due to a large value of the photoelectric current derived by the scale projection. As the result, the intensity of the light through the observing system becomes inadequate to produce a visible target image. In order to avoid the problem, the brightness of the background of the scale projecting system may be decreased. For example, the scales may have dark background and transparent scale indentations.

In order to obtain an exact measurement, it is required to maintain the patient's eye in a condition seeing an infinitely far point. For this purpose, the refractmeter is provided with a viewing mark projecting system which comprises a collimater lens 42 for directing the light from the light source 1 along an optical axis 41 in the form of a parallel light bundle and a viewing mark plate 43 disposed on the optical axis 41. The light bundle through the mark plate 43 is passed through a lens 44, pentagonal prisms 45 and 46 and reflected by a mirror 47 and then through lenses 48 and 49 and the objective lens 12 to the patient's eye 13. Therefore, the measurement is performed by letting the patient's eye observe the projected mark.

Figure 9:
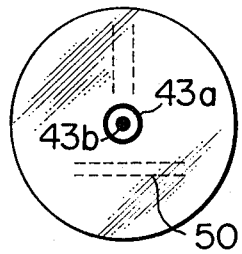
FIG. 9 shows an example of the viewing mark projected together with the target.

In order to avoid the patient's attention being directed to the target image, it is preferable to project the viewing mark 43a by a red light together with the target 50 as shown in FIG. 9. For the purpose, a half-transparent mirror 47a may be provided in lieu of the mirror 47 and located on the optical axis 10 between the image rotating device 14 and the objective lens 12 to project the viewing mark along the axis 10. Further a red filter may be provided in the optical axis 41. As previously described, the target is projected by the infrared ray but, when the wave length of the infrared ray is close to that of visible light, the projected target may be legible to the patient even though the contrast of the target image is very weak. It should be noted, however, that by projecting the viewing mark by a red light, there is produced a red coloured background around the target so that the contrast between the target and the background is extremely weakened and therefore it becomes possible to keep the patient's attention out of the target.

In case where the objective lens 12 is provided with a black spot as shown by 12a on the center of the rear surface in order to prevent the light reflected at the surface from entering the observing optical system, the viewing mark should preferably have a black spot 43b which is large enough and so located to cover the black spot on the objective lens 12 when the black spot 43b is projected. This is effective to keep the patient's attention out of the black spot 12a on the objective lens 12.

In order to accomplish an exact alignment between the objective lens and the patient's eye 13, there may be provided an alignment mark projecting system. As shown in FIG. 5, the system includes an optical axis 123 which is located in a plane passing through the optical axis 10 and perpendicular to the plane containing the observing axis 10 and the sighting axis 19. The system further includes a light source 124 of infrared ray, a condenser lens 125, a mark plate 126, a reflecting mirror 127 and projecting lenses 128 and 129.

Figure 10:
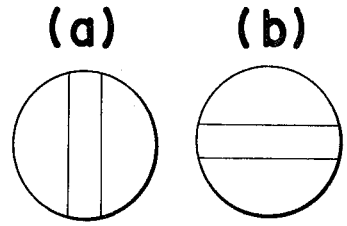
FIGS. 10 (a) and (b) show an example of the alignment mark for establishing a correct alignment between the patient's eye and the objective lens of the refractmeter.

On the mark plate 126, there is a mark, for example, in the form of a pair of parallel lines extending parallelly to the plane containing the axis 10 and 123 as shown in FIG. 10 (a). The mark is thus projected on the patient's eye and focused at the surface thereof. In the sighting optical system, there is provided a mark plate 130 having a mark in the form of a pair of parallel lines extending parallelly to the plane containing the axes 10 and 19. It should thus be understood that a correct alignment is established between the objective lens and the patient's eye by adjusting the refractmeter so that the parallel lines on the mark plate 126 are projected on the patient's eye at the opposite sides of the iris and at the same time the iris is positioned between the parallel lines on the mark plate 130.

The invention has thus been shown and described with reference to specific embodiments, however, it should be noted that the invention is in no way limited to the details of the illustrated arrangements but changes and modifications may be made without departing from the scope of the appended claims.

We claim:

1. An eye refractmeter comprising a target projecting optical system for projecting an image of target means through a pupil of a patient's eye to produce a target image on a retina of the eye, an observing optical system passing a first light beam and including objective lens means for observing the target image through the pupil, a sighting optical system passing a second light beam for observing the cornea of the eye to determine that the objective lens means is appropriately spaced from the patient's eye, said projecting optical system including means for projecting the image of the target means by an infrared ray, half-transparent optical means for passing therethrough one of light beams passing through said observing and sighting optical systems and reflecting the other of the light beams, means for directing both of the light beams passing through said observing and sighting optical systems to a single image pick-up tube, said half-transparent optical means having a reflecting rate such that more than 50% of the light passing through the observing optical system and less than 50% of the light passing through the sighting optical system are directed to the image pick-up tube.

2. An eye refractmeter in accordance with claim 1 in which said half-transparent optical means is so arranged that the light bundle which has passed along the observing optical system is passed through the half-transparent optical means before it is directed to the image pick-up tube.

3. An eye refractmeter in accordance with claim 1 in which said half-transparent optical means has such reflecting rate that it directs approximately 90% of the light passing through the observing optical system and approximately 10% of the light passing through the sighting optical system to the image pick-up tube.

4. An eye refractmeter in accordance with claim 1 in which said target means is movable along an optical axis of the target projecting optical system and a scale projecting system is provided for projecting a scale on the image pick-up tube, said scale representing the position of the target means on the optical axis of the target projecting optical system.

5. An eye refractmeter in accordance with claim 4 in which the target projecting optical system includes means for rotating the target image about the projecting optical axis, said scale projecting optical system further including means for projecting on the image pick-up tube an angular scale representing angle of rotation of the target image.

6. An eye refractmeter in accordance with claim 1 which further includes viewing mark projecting means for projecting viewing mark means in superimposed relationship with the target means by a red ray which is in a form of parallel light beam.

7. An eye refractmeter in accordance with claim 6 in which said objective lens means has a first black spot located at the center of one surface thereof for preventing light reflected at the surface from entering the observing optical system, said viewing mark means including a second black spot which is larger than and covers the first black spot on the objective lens means to divert a patient's attention from said first black spot, said viewing mark projecting means including means for projecting said viewing mark means coaxially through the objective lens means.

8. An eye refractmeter in accordance with claim 1 which further includes an alignment mark projecting system for projecting a first alignment mark on the patient's eye in a first plane perpendicular to a second plane which contains optical axes of said observing and sighting optical systems, said first alignment mark comprising at least one straight line extending parallelly to one of the first and second planes, said sighting optical system having a second mark comprising at least one straight line extending parallelly to the other of the first and second planes.

9. An eye refractmeter comprising a target projecting optical system for projecting an image of a target means through a pupil of a patient's eye to produce a target image on the retina of the eye, an observing optical system including objective lens means having an optical axis for observing the target image through the pupil, and a viewing mark projecting system for projecting a viewing mark coaxially through the objective lens means with a substantially parallel light beam, said objective lens means having a black spot at the optical axis thereof, said viewing mark comprising black pattern which is larger than and covers the black spot to divert a patient's attention from said black spot.

10. An eye refractmeter in accordance with claim 9 in which said viewing mark comprises a central black pattern encircled by a ring.

11. An eye refractmeter in accordance with claim 9 in which said target projecting means includes means for projecting the image of said target means by an infrared ray, and said viewing mark projecting means includes means for projecting the viewing mark by a red light.

12. An eye refractmeter comprising a target projecting optical system for projecting an image of a target means through a pupil of a patient's eye to produce a target image on the retina of the eye, an observing optical system including objective lens means for observing the target image through the pupil, a sighting optical system for observing the cornea of the eye to determine that the objective lens means is appropriately spaced from the patient's eye, and an alignment mark projecting system having an alignment mark projecting axis lying in a first plane which is perpendicular to a second plane including the observing and sighting optical systems, said alignment mark projecting system including a first mark comprised of at least one line parallel to said first plane, said sighting optical system including a second mark comprised of at least one line parallel to said second plane.

13. An eye refractmeter in accordance with claim 12 in which said first and second marks comprise respectively paired parallel lines.

* * * * *